(12) United States Patent
Gie et al.

(10) Patent No.: US 6,383,224 B1
(45) Date of Patent: May 7, 2002

(54) PROSTHETIC ACETABULUM FIXING PLATE

(75) Inventors: Graham Allan Gie, Yeoford; Robin Sydney Mackwood Ling, Darthmouth, both of (GB); John Andrew Storer, Bayeux (FR); Andrew John Timperley, Exeter (GB)

(73) Assignee: Benoist Girard SAS (FR)

( * ) Notice: Subject to any disclaimer, the term of this patent is extended or adjusted under 35 U.S.C. 154(b) by 0 days.

(21) Appl. No.: 09/464,578

(22) Filed: Dec. 16, 1999

(30) Foreign Application Priority Data

Dec. 17, 1998 (GB) ............................................... 9827879

(51) Int. Cl.⁷ .................................................. A61F 2/32
(52) U.S. Cl. ................................................... 623/22.39
(58) Field of Search ........................... 623/22.39, 22.38, 623/22.2–22.25, 22.21, 22.37, 32, 33, 19.12

(56) References Cited

U.S. PATENT DOCUMENTS

| 3,866,248 | A |   | 2/1975  | Kummer ............................. 3/1 |
| 5,030,233 | A | * | 7/1991  | Ducheyne ....................... 623/16 |
| 5,658,338 | A | * | 8/1997  | Tullos et al. ................... 623/18 |
| 5,702,477 | A | * | 12/1997 | Capello et al. ................ 623/22 |
| 5,879,398 | A | * | 3/1999  | Swarts et al. ................. 623/22 |
| 5,888,205 | A | * | 3/1999  | Pratt et al. ...................... 623/23 |
| 5,931,870 | A | * | 8/1999  | Cuckler et al. ................ 623/16 |
| 5,981,828 | A | * | 11/1999 | Nelson et al. ................. 623/16 |

FOREIGN PATENT DOCUMENTS

| DE | 24 10 057 | 7/1975 |
| DE | 28 37 400 | 2/1980 |
| EP | 0 328 847 | 8/1989 |
| EP | 0 834 294 | 4/1998 |
| FR | 2 056 934 | 5/1971 |
| FR | 2 633 823 | 1/1990 |
| GB | 1 430 071 | 3/1976 |

* cited by examiner

Primary Examiner—Corrine McDermott
Assistant Examiner—Alvin Stewart
(74) Attorney, Agent, or Firm—Lerner, David, Littenberg, Krumholz & Mentlik, LLP

(57) ABSTRACT

A prosthetic fixing plate comprises a component to be located into the acetabulum prior to the insertion of a prosthetic ball joint cap. The plate has a closure wall adapted to close the wall or rim of the acetabulum across any discontinuity therein, and a locator is provided for locating said closure wall in place. The fixing plate can be supplied in various sizes and arrangements, the correct plate being chosen by the surgeon after close examination of X-ray photographs of the patient and through the use of a template which is used to determine the size and arrangement of the discontinuity and thus the correct size and arrangement of the plate to be used.

16 Claims, 2 Drawing Sheets

PROSTHETIC ACETABULUM FIXING PLATE

BACKGROUND OF THE INVENTION

1. Field of the Invention

This invention relates to the use of prosthetic ball joint cups in the surgical procedures to replace skeletal joints such as a hip joint.

2. Description of Prior Art

During these procedures, it has been noted that any discontinuity in the rim or wall of the acetabulum of the innominate bone, for example the acetabular notch between the transverse ligament, is instrumental in causing problems where the fixing bone cement used to bond the ball joint cup to the surface of the acetabulum is often lost through the discontinuity. In order to prevent this loss of cement, a fixing plate is placed inside the acetabulum, blocking the discontinuity and allowing the ball joint cup to be pushed into place without loss of cement.

SUMMARY OF THE INVENTION

According to the present invention, a prosthetic acetabulum fixing plate comprises a component to be located into the acetabulum prior to the insertion of a prosthetic ball joint cap. The plate has a closure wall adapted to close the wall or rim of the acetabulum across any discontinuity therein, and a locator element is provided for locating the closure wall in place.

The fixing plate can be supplied in various sizes and arrangements, the correct plate being chosen by the surgeon after close examination of X-ray photographs of the patient and through the use of a template which is used to determine the size and arrangement of the discontinuity and thus the correct size and arrangement of the plate to be used.

The plate can be made from any suitable material but is preferably made from a synthetic plastic material for example polymethylmethacrylate, (P.M.M.A.). Preferably the fixing plate also has a lining portion adapted to extend across the depressed portion of the acetabulum (the fossa). This lining portion can have apertures to enable fixing cement to extend through it.

The plate can be used after a filling material such as bone graft is used to fill the depression in the inner surface of the acetabulum, the acetabular component then being placed over the filling material. The plate can then become a continuation of the substantially continuously circular nature of the outer rim of the acetabulum.

The surface of the closure wall can be adapted to include a location and depth defining element adapted for use in conjunction with an acetabular cup with a disposable flange or a fixed flange or indeed without a flange if the closure wall is adapted to engage the appropriate portion of the cup, so that location and depth defining means are provided for the acetabular cup.

The apertures in the plate face can be of a size consistent with the passage of the fixing cement used to bond a prosthetic ball joint cup into the acetabulum. The plate can be dimensioned in varying size dependent on the patient. The device for locating the plate and closure wall in position may conveniently comprise a clip adapted to extend over the rim of the acetabulum adjacent to any discontinuity.

BRIEF DESCRIPTION OF THE DRAWINGS

The invention can be performed in various ways but one embodiment will now be described by way of example and with reference to the accompanying drawings in which.

DESCRIPTION OF THE PREFERRED EMBODIMENTS

Figure 1:
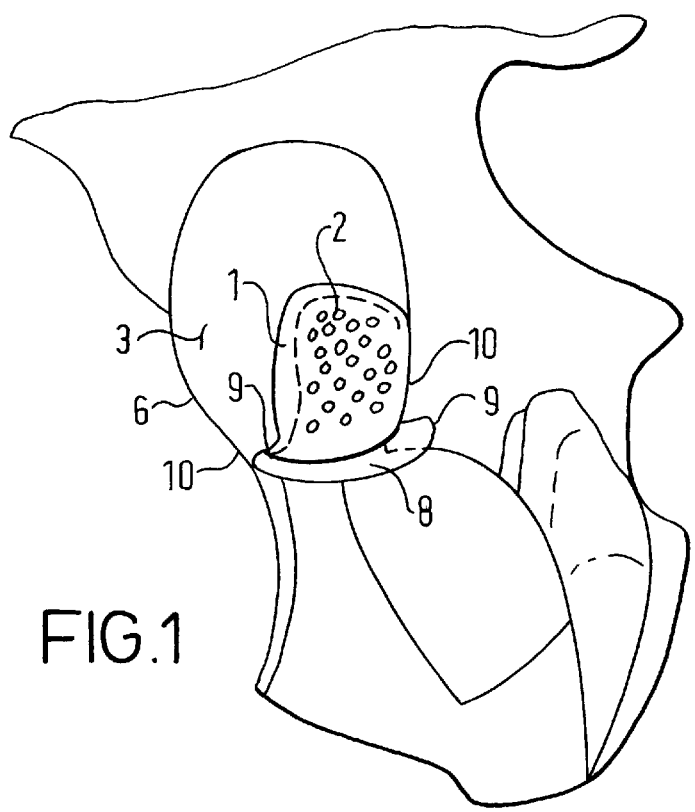
FIG. 1 is a partial front elevation of the innominate bone and the prosthetic acetabulum fixing plate according to the invention.
Figure 2:
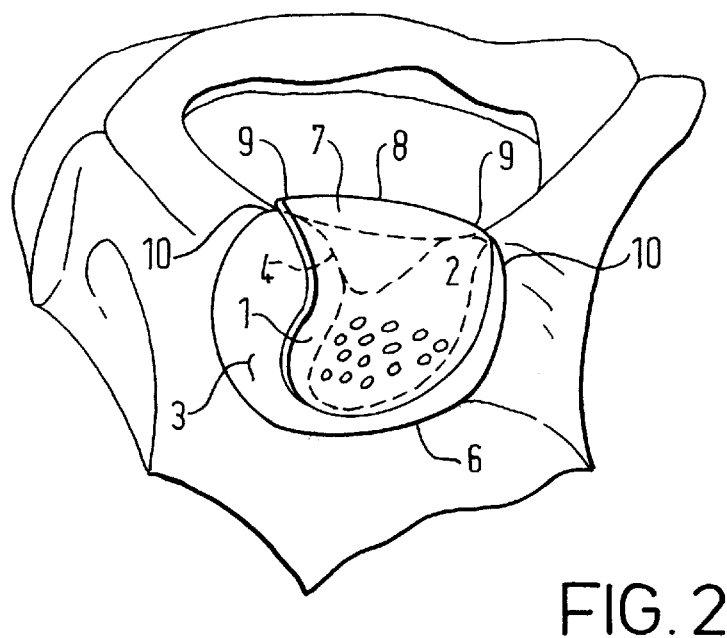
FIG. 2 is a partial isometric view of the innominate bone and the prosthetic fixing plate.

As shown in FIGS. 1–5, a prosthetic acetabulum fixing plate according to the invention comprises a plate 1 having a lining portion which has apertures 2 which is dished to allow it to be located contiguously with the inner surface of the acetabulum 3 covering the discontinuity 4 (see FIG. 2) of the rim 6 of the acetabulum and the depression, or fossa 5 in the inner surface of the acetabulum 3 and having a closure wall portion 7 which extends across the discontinuity 4.

In addition to plate 1 a corresponding amount of bone graft (not shown) is placed into the fossa 5 prior to plate 1 being positioned.

With plate 1 located in position, a corresponding amount of fixing or bone cement (not shown) is placed within the acetabulum 3 and any typical prosthetic ball joint or acetabular cup (not shown) is pushed into place. When the bone cement is pressurized, such as by the device shown in copending application Ser. No. 09/184,539 entitled Acetabular Cup Cement Pressurization Device, it passes through the apertures 2 in the plate and mixes with the bone graft (not shown) in the depression 5 of the acetabulum thus bonding the prosthetic fixing plate 1 and the cup into position.

To assist in locating the plate closure wall 7 is extended to form a reentrant clip 8 each spaced apart outer end 9 of which engages over the rim portion 10 of the acetabulum 3 at each side of discontinuity 4. This clip 8 enables plate 1 to be firmly located prior to insertion of cement (not shown) and the acetabulum cup which is to be secured.

Figure 3:
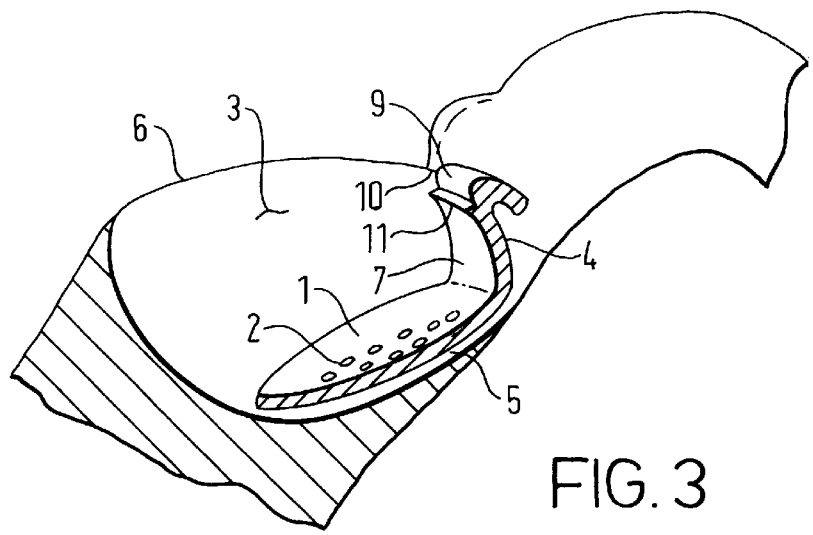
FIG. 3 is a partial isometric cross section of the innominate bone and a second embodiment of the prosthetic fixing plate.
Figure 4:
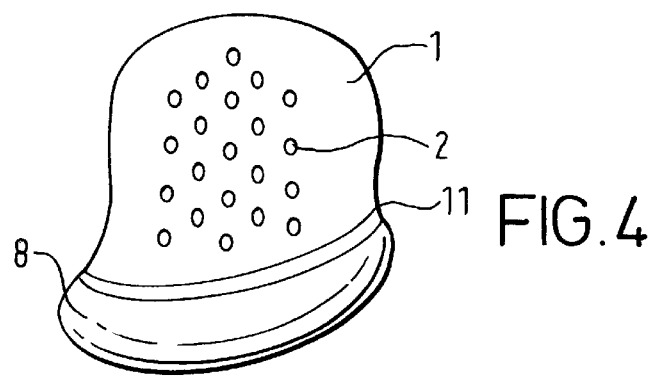
FIG. 4 is a plan view of the second embodiment of the prosthetic acetabulum fixing plate as shown in FIG. 3.
Figure 5:
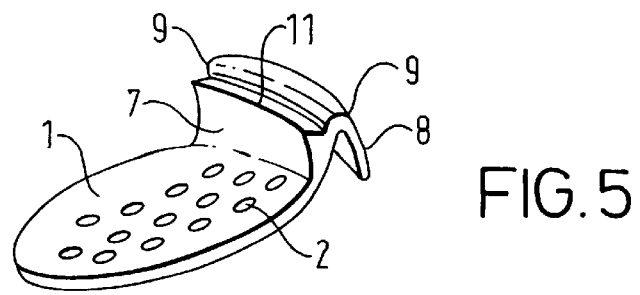
FIG. 5 is an isometric view of the prosthetic acetabulum fixing plate shown in FIG. 4.

With reference to the embodiment shown in FIGS. 3–5, it can be seen that a ridge or ledge cement 11 can be included in the surface of closure wall 7 to provide a location and depth defining means for a prosthetic acetabular cup (not shown) provided with a flange, or a rim, for example as described and shown in U.S. Pat. No. 6,019,766, which will be inserted into the acetabulum after fixing plate 1 has been properly located. The rim or flange on the acetabular cup extends circumferentially around an outer surface of the cup. The rim or flange engages ledge 11 to locate, at least depth wise, the acetabular cup in the prepared acetabulum.

What is claimed is:

1. A method for implanting an acetabular cup in the opening in a prepared acetabulum comprising:

placing a plate contoured to the shape of the prepared acetabulum over at least part of a rim of the acetabulum, said plate having a plurality of openings therein for allowing bone cement to pass therethrough;

placing bone cement in the prepared acetabulum either before or after placing said plate in the acetabulum; and placing the acetabular cup in said prepared acetabulum with said plate in place said plate having a ledge formed thereon extending radially inwardly of said rim into the opening at a point below the plane of said opening having a surface facing the opening of said acetabulum.

2. The method as set forth in claim 1, wherein bone graft is placed into the prepared acetabulum prior to placing the plate therein.

3. The method as set forth in claim 1, wherein said plate includes a clip portion for engaging an outer rim portion of the acetabulum.

4. A prosthetic acetabulum fixing plate comprising a body to be located in the acetabulum prior to the insertion of a prosthetic ball joint cup, said body having a closure wall adapted to close a wall or rim of the acetabulum across any discontinuity therein, and a locating element for locating said closure wall in place said plate having a ledge formed thereon extending radially inwardly of said rim into the opening at a point below the plane of said opening having a surface facing the opening of said acetabulum.

5. The prosthetic acetabulum fixing plate as claimed in claim 4 in which said closure wall is made from synthetic plastics material.

6. The prosthetic acetabulum fixing plate as claimed in claim 5 in which said synthetic plastics material is polymethylmethacrylate.

7. The prosthetic acetabulum fixing plate as claimed in claim 4 which has a lining portion adapted to extend across the depressed portion of the acetabulum (the fossa).

8. The prosthetic acetabulum fixing plate as claimed in claim 7 in which said lining portion has apertures to enable bone cement to pass through it.

9. The prosthetic acetabulum fixing plate as claimed in claim 8 in which the ledge surface of the closure wall is adapted to include location and depth defining element adapted for use in conjunction with an acetabular cup to locate the cup.

10. The prosthetic acetabulum fixing plate as claimed in claim 9 in which apertures are provided in the plate face which are a size consistent with the passage of bone cement used to bond a prosthetic ball joint cup into the acetabulum.

11. The prosthetic acetabulum fixing plate as claimed in claim 4 in which apertures are provided in the plate face which are of a size consistent with the passage of the bone cement used to bond a prosthetic ball joint cup into the acetabulum.

12. The prosthetic acetabulum fixing plate as claimed in claim 4 in which the means for locating the plate and closure wall in position comprise a clip adapted to extend over the rim of the acetabulum adjacent to any discontinuity.

13. A liner for the acetabulum to facilitate implantation of an acetabular cup into an opening of the acetabulum comprising:

a plate made of synthetic plastics material having a plurality of apertures therethrough;

a clip portion preformed along a portion of a circumferential wall of said plate, said clip forming a resilient generally U-shaped cavity for engaging a rim of the acetabulum said plate having a ledge formed thereon extending radially inwardly of said rim into the opening at a point below the plane of said opening having a surface facing the opening of said acetabulum.

14. The prosthetic acetabulum fixing plate as claimed in claim 13 in which said synthetic plastics materials is polymethylmethacrylate.

15. The prosthetic acetabulum fixing plate as claimed in claim 14 in which the ledge surface of the closure wall is adapted to include location and depth defining element adapted for use in conjunction with an acetabular cup to locate the cup.

16. The prosthetic acetabulum fixing plate as claimed in claim 13 in which apertures are provided in the plate face which are a size consistent with the passage of bone cement used to bond a prosthetic ball joint cup into the acetabulum.

* * * * *